United States Patent [19]

Eckler

[11] Patent Number: 4,912,187

[45] Date of Patent: Mar. 27, 1990

[54] SOLID ESTER PRODUCTS OF STERICALLY HINDERED POLYHYDROXYMONOCARBOXYLIC ACIDS

[75] Inventor: Paul E. Eckler, Terre Haute, Ind.

[73] Assignee: Questra Chemicals Corp., Atlanta, Ga.

[21] Appl. No.: 149,440

[22] Filed: Jan. 29, 1988

[51] Int. Cl.$^4$ .............. C08G 63/00; C08G 63/16; C07C 69/66

[52] U.S. Cl. .................. 527/604; 528/302; 560/186

[58] Field of Search .......... 528/302; 560/186; 524/317; 527/604

[56] References Cited

U.S. PATENT DOCUMENTS

| | | | |
|---|---|---|---|
| Re. 30,612 | 5/1981 | Harris et al. | 260/22 TN |
| 2,089,127 | 8/1937 | Lock | 560/189 |
| 2,488,303 | 11/1949 | Mack | 560/189 |
| 2,527,057 | 10/1950 | Canfield | 527/604 |
| 3,345,313 | 10/1967 | Ruhf | 528/303 |
| 3,345,339 | 10/1967 | Parker | 528/283 |
| 3,404,018 | 10/1968 | Hicks | 106/252 |
| 3,441,953 | 4/1969 | Dumont | 560/189 |
| 3,583,942 | 6/1971 | Malek | 528/275 |
| 3,658,939 | 4/1972 | Carpenter | 524/288 |
| 3,669,939 | 6/1972 | Baker . | |
| 3,707,526 | 12/1972 | Gannon | 528/361 |
| 3,741,941 | 6/1973 | Ashe | 528/354 |
| 3,759,873 | 9/1973 | Hudak | 528/80 |
| 3,787,370 | 1/1974 | Shima | 528/274 |
| 3,792,112 | 2/1974 | Gannon | 525/514 |
| 3,882,189 | 5/1975 | Hudak | 528/303 |
| 4,046,739 | 9/1977 | Lacona | 528/272 |
| 4,093,595 | 6/1978 | Elliott | 528/279 |
| 4,133,786 | 1/1979 | Harris et al. | 525/7 |
| 4,166,149 | 8/1979 | Mueller | 428/339 |
| 4,289,874 | 9/1981 | Bockrath | 528/494 |
| 4,314,918 | 2/1982 | Birkmeyer | 528/161 |
| 4,320,222 | 3/1982 | Lopez | 528/89 |
| 4,356,285 | 10/1982 | Kumagai | 525/111 |
| 4,398,034 | 8/1983 | Edmonson et al. | 528/307 |
| 4,447,567 | 5/1984 | Geerdes | 523/501 |
| 4,496,487 | 1/1985 | Peerman | 260/404 |
| 4,528,356 | 7/1985 | Allen | 528/89 |
| 4,622,117 | 11/1986 | Geist | 204/181.7 |
| 4,649,082 | 3/1987 | Friedlander | 428/461 |
| 4,694,033 | 9/1987 | van der Linde | 527/604 |
| 4,798,859 | 1/1989 | Höhlein et al. | 525/7 |

OTHER PUBLICATIONS

W. J. Van Westrenen, "Modern Developments in Aqueous Industrial Coatings" 62 J. Oil Col. Chem. Assoc. 246-255 (1979).

IMC/Pitman-Moore, "A Complete Guide to DMPA Brand of Dimethylopropionic Acid," Revised Edition 1987.

Primary Examiner—Harold D. Anderson
Assistant Examiner—Dennis R. Daley
Attorney, Agent, or Firm—Banner, Birch, McKie & Beckett

[57] ABSTRACT

An ester of a sterically hindered polyhydroxymonocarboxylic acid and a polyhydroxy-containing component, which ester is a solid at ambient temperature conditions, comprising the condensation product of said acid selected from the group consisting of dimethylolpropionic acid, trimethylolacetic acid, and mixtures thereof, and said polyhydroxy-containing component selected from the group consisting of pentaerythritol, trimethylolethane, and mixtures thereof, said product having a mol ratio of acid to polyhydroxy-containing component of at least about 1.75, a ring and ball softening point of at least about 50° C., and an acid number of less than about 40.

An ester of a sterically hindered polyhydroxymonocarboxylic acid and a polyhydroxy-containing component, which ester is a solid at ambient temperature conditions, comprising the condensation product of said acid selected from the group consisting of dimethylolpropionic acid, trimethylolacetic acid, and mixtures thereof, and pentaerythritol, said product having a mol ratio of acid to pentaerythritol of at least about 0.75, a ring and ball softening point of at least about 50° C., and an acid number less than about 40.

An ester of trimethylolacetic acid and trimethylolpropane, which ester is a solid at ambient temperature conditions, comprising the condensation product of said acid and said trimethylolpentane, said product having a mol ratio of acid to trimethylolpentane of at least about 1.75, a ring and ball softening point of at least about 50° C., and an acid number of less than about 40.

27 Claims, No Drawings

SOLID ESTER PRODUCTS OF STERICALLY HINDERED POLYHYDROXYMONOCARBOXYLIC ACIDS

BACKGROUND OF THE INVENTION

1. Field of the Invention

This invention relates to solid resinous products which are esters of hindered carboxylic acids. More specifically, the invention relates to solid ester products which have high degree of hydroxyl functionality.

2. Description of Related Art

Use of resins in diverse commercially important applications is well-established. The ability to prepare resins which have preselected properties has increased the acceptance of such materials in many applications. However, the physical form of some resins often makes them difficult to distribute in commerce. Many such resins are highly viscous liquids or gelatinous semi-solids, neither of which is conveniently transported. Resins having both a high proportion of hydroxyl functionality and a conveniently-transported physical form have not been made widely available.

Resinous compounds are useful, inter alia, in lacquers, waxes, and other protective coatings; for textile finishing treatments; and as binders for particulate matter. However, many resin products are difficult to prepare and handle.

Ester products having hydroxyl substituents made by the condensation of unhindered carboxyl-functional constituents with hydroxyl-functional constituents (polyols) are well known in the art. Such ester products are available from diverse sources. Examples of such products are those described in U.S. Pat. No. 2,488,303, which discloses the esterification of organic acids with glycols. However, these products do not provide the required combination of product characteristics such as ease in handling and desired high hydroxyl functionality.

One approach for increasing the hydroxyl functionality of ester products involves using a hydroxyl-substituted carboxylic acid for reaction with the polyol. However, the carboxyl group on such hydroxyl-substituted acids is often sterically hindered and esterification of such sterically hindered carboxylic acids is significantly more difficult than esterification of the unhindered carboxylic acids such as the esterification described in U.S. Pat. No. 2,488,303. Known techniques for the esterification of hindered carboxylic acid moieties typically require use of strong acid catalysts, so the variety of such esters is limited. Therefore, the ester products of sterically hindered carboxylic acids are not well known and not easily obtained.

Ungelled resins suitably cured by exposure to ionizing radiation or ultraviolet light are disclosed in U.S. Pat. No. 4,649,082. The resins comprise esters which are the reaction product of a polyfunctional hydroxy-containing carboxylic acid, a hydroxyl-functional compound, and an unsaturated carboxylic acid. The esters may be prepared in one- or two-step processes. In the latter, it is broadly disclosed that the polyfunctional hydroxy-containing carboxylic acid having a molecular weight less than 1000 (one example being dimethylolpropionic acid) can be reacted with an organic hydroxyl-functional compound, such as a diol, at a molar ratio of anywhere between about 3:1 to 0.5:1, preferably between 2:1 to 1.5:1, and at a temperature between about 150° and 220° C. Typically, an esterification catalyst, such as butyl stannoic acid, dibutyltin oxide, antimony oxide, dibutyltin dilaurate, paratoluenesulfonic acid, and methane sulphonic acid is utilized. However, the physical characteristics of these esters are not reported. In the illustrated examples, dimethylolpropionic acid is reacted with diethylene glycol, 1,4-butanediol, cyclohexanedimethanol, and dipropylene glycol, all at molar ratios of acid to polyol of 2:1. No information about the physical characteristics of the ester products is provided.

The self-condensation product of a polyhydroxymonocarboxylic acid is disclosed in U.S. Pat. No. 3,669,939. Small amounts of other such acids, monohydroxy compounds, monocarboxylic compounds, and polyhydroxy compounds also may be co-condensed but their presence is undesired. Only the self-condensation products of poly-functional (i.e., hydroxycarboxylic compounds) constituents are exemplified.

U.S. Pat. No. 3,441,953 discloses the esters of dimethylolpropionic acid with various ethylene glycols. Esters prepared at a 1:1 molar ratio of dimethylolpropionic acid with triethylene glycol (molecular weight 150) and with polyethylene glycol-300 (PEG 300-i.e., PEG having an approximate molecular weight of 300) are described as oily liquids. Using heavier PEG's yields products which range from pasty solids to waxy semi-solids which melt in one's hand.

It is an object of this invention to provide new esters of sterically hindered polyhydroxy monocarboxylic acids.

It is a further object of this invention to provide new esters of sterically hindered polyhydroxymonocarboxylic acids which provide a high degree of hydroxyl functionality.

It is another object of this invention to provide new esters of sterically hindered polyhydroxymonocarboxylic acids, which esters are sufficiently solid to be conveniently transported in commerce as prills, granules, powder, or in other durable forms.

It is yet another object of this invention to provide a method of preparing these esters.

It is a still further object of this invention to provide alkyd and polyester resins made using these esters.

SUMMARY OF THE INVENTION

In accordance with these and other objects, this invention relates to solid products which are esters of hindered polyhydroxy monocarboxylic acids. These solid products have a high degree of hydroxyl functionality, so that they may be called synthetic polyols. These synthetic polyols are useful as intermediates in the preparation of synthetic lubricant esters, rosin esters, printing inks, and in the preparation of alkyd and polyester resins.

DETAILED DESCRIPTION OF THE INVENTION

This invention is based on the discovery that certain esters of hindered carboxylic acids are sufficiently solid under ambient temperature conditions to be handled as prills, granules, powder, flakes, chips, or other conveniently handled solid forms. These esters are the condensation products of certain sterically hindered carboxylic acids and particular polyols, giving them a sufficiently high degree of hydroxyl functionality so that they are called synthetic polyols. The chemical characteristics of these synthetic polyols make them suitable for use as intermediates in the preparation of synthetic lubricant esters, rosin esters, printing inks, and in the preparation of alkyd and polyester resins.

Esters which are the subject of this invention are the condensation products of pentaerythritol or trimethylolethane with dimethylolpropionic acid or trimethylolacetic acid, and the condensation products of trimethylolprpane with trimethylolacetic acid. These esters are prepared in accordance with the process described below. These resinous polyols are solid at ambient temperature conditions and are suitable for various uses, some of which are described above. As used herein, the term "ambient temperature conditions" means a temperature between about 10° C.–40° C. When used as an intermediate in the production of rosin esters, alkyd and polyester resins, and the like, the products of this invention may be reacted with oils, fatty acids, and other constituents which will give an ultimate product the desired properties.

The mol ratio of polyhydroxymonocarboxylic acid to polyol is selected to produce desired physical and chemical characteristics of the resulting ester. Solid resin of the invention is obtained when the mol ratio of polyhydroxymonocarboxylic acid i.e., dimethylolpropionic acid, trimethylolacetic acid, and mixtures thereof, to pentaerythritol is greater than about 0.75:1, preferably is between 0.75:1 and 100:1, more preferably between about 0.75:1 and 20:1, and most preferably is between about 0.75:1 and 2.5:1.

Trimethylolethane-containing esters of the invention require that the ratio of polymethylolalkanoic acid (dimethylolpropionic acid, trimethylolacetic acid, and mixtures thereof) to trimethylolethane be greater than about 1.75:1, preferably between about 1.75:1 and 100:1, more preferably between about 1.75:1 and 20:1, and most preferably between about 1.75:1 and 2.5:1.

Esters of the invention containing the ester product of trimethylolpropane and trimethylolacetic acid are prepared by reacting at least about 1.75 mols of acid per mol of polyol, preferably between about 1.75 and 100, more preferably between about 1.75 and 20, and most preferably between about 1.75 and 2.5, mols of trimethylolacetic acid per mol of trimethylolpropane.

Products of this invention are prepared by reacting a polyhydroxymonocarboxylic acid with a polyol in the presence of a catalyst. This reaction may take place in the presence of solvent. The carboxylic acid moiety is esterified with one hydroxyl moiety from the polyol. Esterification is an equilibrium reaction, and thus is affected by the concentration of water in the reactant mixture. If solvent is utilized, water of condensation is removed by azeotropic distillation with the solvent. Otherwise, the water of condensation evaporates at reaction conditions and is removed from the reactant mixture to ensure favorable reaction conditions.

The carboxylic acid moiety of a polyhydroxymonocarboxylic acid is sterically hindered by, inter alia, hydroxyalkyl groups pendant from the quaternary carbon, i.e., the carbon to which the carboxyl group is attached. These hydroxyalkyl groups limit the ability of the carboxyl moiety to react chemically with polyols because they prevent reactive molecules from coming sufficiently close to react. Therefore, esterification of the group is difficult and normally require severe reaction conditions.

Minor quantities of other reactants, typically less than 20% based on the total reaction mixture, may be incorporated into the synthetic polyol molecule. Known alkyd and polyester resin precursors are suitable. These components include dibasic acid such as phthalic anhydride, phthalic acid, isophthalic acid, terephthalic acid, maleic anhydride, succinic anhydride, adipic acid, azelaic acid, sebacic acid, dimer acid, and the like; monobasic acids, such as tall oil fatty acid, soybean fatty acid, linseed oil fatty acid, benzoic acid, p-t-butylbenzoic acid, hexanoic acid, heptanoic acid, octanoic acid, pelargonic acid, decanoic acid, 2-ethylhexanoic acid, lauric acid, rosin; fatty acids derived from other glycerine oils such as castor oil, coconut oil, sunflower oil, cotton seed oil, safflower oil, fish oil, and the like; and monoglycerides, which are obtained by the alcoholysis of glycerine triesters with polyols or the acidolysis of glycerine triesters with dibasic acids, as is well known in the alkyds industry.

An active sterically hindered carboxylic acid esterification catalyst is used in the method of this invention. Any such catalyst, such as stannous chloride, stannic chloride, tetrabutyl titanate, dibutyl tin oxide, para-toluenesulfonic acid, and the like, can be used in this method. The amount of catalyst typically exceeds 0.01 wt. percent based on the weight of reactants, and is limited at its upper end only by the economic considerations. Preferably, between about 0.01–1.0, more preferably between about 0.05 and 0.5 wt. percent, and most preferably between about 0.08 and 0.13 wt. percent catalyst is used.

The activity of tin-containing catalysts is believed to be related to the concentration of tin in the compound. Therefore, for a given quantity of tin-containing catalyst, stannous chloride has the highest activity, stannous oxalate and octoate the lowest.

The activity of these catalysts makes it possible to esterify hindered carboxylic acids at temperatures above 80° C. The reaction temperature should remain below the decomposition temperature of the reactants. Within this range, the reaction temperature should be maximized to take advantage of the improvement in reaction rate as temperature is increased. For example, dimethylolpropionic acid decomposes at about 225° C. at atmospheric pressure. Therefore, the preferred range of reaction temperatures for the esterification of dimethylolpropionic acid is 80°–220° C., more preferably between about 150°–220° C., and most preferably between about 200°–220° C. Those skilled in the art will be able to determine the appropriate corresponding temperature ranges for trimethylolacetic acid.

The pressure which the reaction proceeds is up to about 20 atmospheres, preferably up to about 1.5 atmospheres. Pressures at the high range may be necessary to minimize loss of volatile reactants, while vacuum may be utilized to increase reaction rate by removing of water of condensation if the reactants and products have low volatility. Those skilled in the art are familiar with such adjustments.

Reaction of the polyhydroxymonocarboxylic acid and polyol typically is carried out under an inert atmosphere. Suitable inert atmospheric components include nitrogen and carbon dioxide. The reaction is allowed to continue until the acid number is reduced to less than about 40, preferably to less than about 20, and more preferably to less than about 10.

Acid number, also referred to as acid value, is the number of milligrams of potassium hydroxide (KOH) required to neutralize the acid moieties in one gram of ester. The value is determined by methods known to skilled practitioners. Typically, a weighted sample of ester is dissolved in a neutral solvent and is titrated with 0.1N potassium hydroxide in methanol to a phenolphthalein end point. The neutral solvent is selected in accordance with the nature of the ester sample.

The products of the invention are recovered from the reaction vessel. Because the water of condensation is removed during reaction, only the desired product remains in the vessel. Molten resins may be filtered if desired to remove traces of insoluble material. The product then is cooled. If appropriate, the melt is applied to a chilled metal roller to prepare flaked resinous produts suitable for bagging. Other methods of handling are known to those skilled in the art.

Polyester resins produced in accordance with the method of the invention may be modified with oils and fatty acids to produce alkyd resins. Methods for producing such alkyd resins are known in the art. These oils, fatty acids, and other alkyd resin components may be incorporated into the resins of the invention in a prepolymer comprising, for example, the polyol component. This prepolymer, a reaction product of fatty acid, polyol, and polybasic acid, is itself a polyol, as it is a hydroxyl-terminated molecule.

Suitable fatty acids include monobasic acid such as tall oil fatty acid, soybean fatty acid, linseed oil fatty acid, octanoic acid, pelargonic acid, decanoic acid, lauric acid, rosin, and the fatty acids derived from other glycerine oils such as castor oil, coconut oil, sunflower oil, cotton seed oil, safflower oil, fish oil, and the like; and monoglycerides, which are obtained by the alcoholysis of glycerine triesters with polyols or the acidolysis of glycerine triesters with dibasic acids, as is well known in the alkyd art.

Other monobasic acids include 8/10 acid (a blend of octanoic and decanoic acids available from Emery Chemical), 12-hydroxystearic acid, isostearic acid, linoleic acid, myristic acid, neodecanoic acid, neopentanoic acid, oleic acid, palmitic acid, stearic acid, and tallow fatty acid.

Suitable oils include animal grease, canola (rape seed oil), castor, dehydrated castor, hydrogenated castor, coconut, corn, cottonseed, fish, lard, linseed, oiticica, palm kernel, peanut, perilla, safflower, soya, sunflower, tallow, tung, and walnut.

Other suitable oils and fatty acids are known to practitioners of the art. Those skilled in the art recognize that blend of these components may also be used.

The products of this invention have a ring and ball softening point, measured by ASTM method E-28, of at least about 50° C. The softening point must, of course, be less than the reaction temperature typically, 230° C., where the reaction mixture will solidify as the ester is formed. The solidity of the product is related to the softening point; generally the higher the softening point, the harder the product. Thus, the ring and ball softening point of the products of the invention preferably is between about 50° and 230° C., more preferably is between 50° and 200° C., and most preferably is between about 100° and 200° C.

The following examples are intended to illustrate the invention and to augment the disclosure, and should not be considered to limit the invention in any way. The invention is limited only by the scope of the appended claims.

EXAMPLE 1

The method of the invention was utilized to prepare various esters; the identifies of the components are provided in Table 1 below. A mixture of the components was heated to 220° C. under a nitrogen atmosphere unless otherwise noted. Each of the products was a hard ester.

TABLE 1

| Example | Acid Name | Grams | Polyol Name | Grams | Catalyst Name | Grams | Comment |
|---|---|---|---|---|---|---|---|
| A | DMPrA | 258 | PE | 277 | BSA | 1.5 | |
| B | DMPrA | 378 | TME | 173 | BSA | 1.5 | |
| C | DMPrA | 356 | PE | 192 | BSA | 1.5 | |
| D | DMPrA | 268 | PE | 288 | BSA | 1.5 | 148 g PhTh |
| E | DMPrA | 514 | PE | 55 | BSA | 1.5 | Tech PE; Acid Value 31.4 |

Key for Table 1
DMPrA Dimethylolpropionic Acid
TME Trimethylolethane
PE Pentaerythritol
BSA Butyl Stannoic Acid (Fascat 4100 ®)
PhTh Phthalic Anhydride The properties of these examples are summarized in Table 2. Ring and ball softening points were determined by ASTM method E-28. Viscosities, determined on an ICI cone and plate viscometer, are reported in the form X/Y/Z, wherein X equals scale reading (0–10), Y is range of scale (10, 40, and 100 poise—same as cone identification number) and Z is temperature, °C., at which the viscosity was determined.

TABLE 2

| Example | R & B, °C. | ICI Data | Color |
|---|---|---|---|
| A | 108–110 | 6.0/40/100; 5.3/100/100 | |
| B | 98 | 5.6/40/100; 2.9/100/100 | |
| C | 95 | >10/40/100; 7.2/100/100 | Low |
| D | 62 | >10/40/100; >10/100/100; 8.2/100/125; 1.8/100/150 | |
| E | 79–80 | 5.3/40/150; >10/40/125 | |

EXAMPLE 2

A resin of the invention was prepared in a 4 L resin flask equipped with an overhead stirrer, a Dean-Stark trap receiver, and nitrogen purge. Technical grade pentaerythritol (1661.4 grams containing 12 percent dipentaerythritol and having an equivalent weight of 36.0 (11.5 mols total)) was charged to the flask, followed by 1545.6 grams (11.5 mols) dimethylolpropionic acid. Thus, the mol ratio of dimethylolpropionic acid to pentaerythritol was 1.0 at the beginning of the reaction, and stayed essentially constant during reaction.

Under nitrogen atmosphere, the solid reactants were heated slowly to avoid charring until a sufficient quantity of the reactants had melted and stirring could begin (about 120° C.). Then, 9 grams of Fascat ® 4100 (butyl stannoic acid) was added. The temperature was increased to 215° C. and reaction was continued until the acid number was reduced to 8.7 (approximately 2.5 hours after addition of catalyst). The acid number, measured in milligrams of potassium hydroxide required to neutralize the acid moieties in one gram of resin, was determined by dissolving a weighed sample in a 1:1 (volume) mixture of toluene and isopropanol and titrating with 0.1N potassium hydroxide in methanol to a phenolphthalein end point. The resin had a ICI viscosity of 1.0 (determined with a 40 cone at 125° C.).

The hot resin was poured into a pan lined with aluminum foil and cooled over night. It set to an off-white solid having a ring and ball softening point of about 108°–110° C.

The Pensky-Martens flash point of the product was determined to be greater than 400° F. The infra-red spectrum indicated a hydroxyl-rich ester with a carbonyl band at 1730 cm$^{-1}$. The hydroxyl content of the sample was determined by ASTM method D-2195 as 31.2 percent, versus 33.7 percent theoretical. The phthalate ester color, also by ASTM method D-2195, was APHA 250. Analysis by a vapor phase chromatography indicated a mixture containing approximately 19 percent by weight unreacted pentaerythritol.

Two elemental analyses were performed. As summarized in Table 3 below, the elemental analyses compare well with the theoretical composition.

TABLE 3

| Component | Elemental Analyses (weight percent) 1 | 2 | Theoretical (weight percent) ($C_{10}H_{20}O_7$) |
|---|---|---|---|
| Carbon | 47.2 | 47.3 | 47.6 |
| Hydrogen | 7.8 | 7.8 | 8.0 |
| Oxygen | 44.1 | 44.1 | 44.4 |
| Residue | 0.3 | 0.1 | — |

X-ray powder defraction showed the product to have considerable amorphous character, but detectable bands were found as follows:

Angle 2-theta (relative intensity, $I_0/I_{max}$ percent): 17.4 (100), 18.1 (41.12), 19.7 (51.89), 20.6 (8.14), 29.4 (41.85), 34.4 (14.12), 35.6 (10.74), 44.6 (6.46), 72.5 (12.67).

This example shows that the resin of the invention is solid at ambient conditions and has a composition very close to predicted.

EXAMPLE 3

Three-hundred sixty grams of the resin prepared in Example 2 were charged into a flask with a steam-heated partial condenser in addition to the equipment described in Example 2. To the flasks were added 1241 g pelargonic acid (Celanese), 2.5 g barium acetate and 7.5 g calcium acetate (catalysts), and 25 mL toluene. The mixture was heated and stirred to a pot temperature of 220° C. until the acid value fell to less than 40 (a relatively high value due to excess pelargonic acid). The excess pelargonic acid was distilled out at high vacuum without a column to a liquid temperature of 180° C. at 0.75 torr. The acid value of the remaining resin, an oil, was 11.3. The oil was diluted with 500 mL ethyl acetate and washed repeatedly with water and saturated sodium bicarbonate. The acid value of the wet oil was reduced to 1.7. The ethyl acetate and water were removed from the oil, first, by rotoevaporation, then by stripping at high vacuum to a liquid temperature of 180° C. at 0.45 torr. The acid value of the oil was 0.76.

The oil was treated with 6 g Darco G-60 powdered charcoal and 2 g neutral aluminum oxide (Aldrich) for one hour at 100° C., a typical treatment regime known in the art. Then 10 g of anhydrous magnesium sulfate was added to remove residual water. The mixture was stirred at room temperature for 1.5 hours. The solids were removed by suction filtration through Whatman No. 2 filter paper. The final product was a light colored oil of acid value of 0.76.

The pour point of the oil was determined by cooling the oil in a dry ice/isopropanol bath unit it solidified, then allowing the solid oil to warm slowly until the sample liquified and would again flow. The sample liquified at 30° to 35° F.

Kinematic viscosities were measured by Industrial Testing Laboratories of St. Louis: 85.6 cs at 100° F. and 11.1 cs at 212° F. Brookfield viscosity was 10.8 mpas/100° C., and the density was 0.9762 g/mL at 25° C. The hydroxyl content was 0.09% (ASTM D2195), and the oil had a Gardner color of 1.

EXAMPLE 4

To compare resins prepared with the product of the invention to resins prepared with commercially available products, the following resin products were prepared.

A. Resin of Dipentaerythritol

An apparatus was assembled consisting of a 4-L resin flask with a stainless steel stirrer, a 2 in. foam breaker bar mounted above the liquid layer, a cork for a bearing, and nitrogen inlet (above the liquid surface), but with open ports rather than condenser and receiver. To the pot was charged 1738.6 g of fresh SylvaRos 20 tall oil rosin. The rosin was heated to 170° C. Then 100 g maleic anhydride was added. The temperature was increased to 205° C. and held for two hours. Then 271.6 g dipentaerythritol and 3.0 g magnesium oxide catalyst were added and the temperature was increased to 260° C. The cook was continued to an acid value of 34.8, requiring 12.5 h cooking over a three-day period. The resin was cooled to 230° C. and then poured into a foil lined metal pan and allowed to cool. After overnight cooling, the solidified product was broken up and bottled.

B. Rosin Ester of the Invention

The rosin ester of the hard resin was prepared as in Part A using 1673.6 g rosin, 100.0 g maleic anhydride, 314.0 g of the hard resin of Example 2, and 3 g magnesium oxide. The final acid value of the product was 36.8.

C. Commercial Resin Ester

Reichold Chemicals Beckasite 43-142 ® is identified by that company as a tripentaerythritol ester.

Ball and ring softening points were determined by ASTM Method E-28, method 8, using apparatus supplied by Fisher Scientific as catalog no. 01-551 with an ASTM 16 C thermometer. The method was calibrated using a commercially available tripentaerythritol product for which ring and ball softening points are reported.

Solvent tolerance was determined by titrating 10 mL of a 60% solids solution of the rosin esters in xylene with the low polarity solvents listed in Table 2 until newsprint could no longer be read through the bottom of the beaker. The xylene solutions were prepared by refluxing as needed and were adjusted to 60% solids based on ASTM NVM (non-volatile material) determinations. The titration solvents were odorless mineral spirits (less than 2% aromatic content), Magie Oil 470, and reagent grade hexanes.

TABLE 4

Comparison of Hard Resin To Other Products

| Rosin Ester | Dipentaerythritol | Hard Resin | Beckasite 43-142 |
|---|---|---|---|
| Softening Point Ball and Ring, °C. | 138 | 127 | 138-39 (as tested) 135-45 (product specification) |
| Solvent tolerance | | | |
| Xylene solution Gardner viscosity | F | D-E | C |
| Magie Oil 470 | 61.7 | 42.6 | 120+ |
| Mineral Spirits | 30.1 | 24.6 | 38.2 |
| Hexanes | 33.5 | 28.9 | 44.3 |

Although preferred embodiments of this invention have been discussed herein, those skilled in the art will appreciate that changes and modifications may be made without departing from the spirit of this invention, as defined in and limited only by the scope of the appended claims.

I claim:

1. An ester of a sterically hindered polyhydroxymonocarboxylic acid and a polyhydroxy-containing component, with ester is a solid at ambient temperature conditions, comprising the condensation product of said acid selected from the group consisting of dimethylolpropionic acid, trimethylolacetic acid, and mixtures thereof, and said polyhydroxy-containing component selected from the group consisting of pentaerythritol, trimethylolethane, and mixtures thereof, said product having a mol ratio of acid to polyhydroxy-containing component of at least about 1.75, a ring and ball softening point of at least about 50° C., and an acid number of less than about 40.

2. The ester of claim 1 wherein the mol ratio is between about 1.75 and 20.

3. The ester of claim 2 wherein the mol ratio is between about 1.75 and 2.5.

4. The ester of claim 3 wherein the ring and ball softening point is between about 100° and 200° C.

5. An ester of a sterically hindered polyhydroxymonocarboxylic acid and a polyhydroxy-containing component, which ester is a solid at ambient temperature conditions, comprising the condensation product of said acid selected from the group consisting of dimethylolpropionic acid, trimethylolacetic acid, and mixtures thereof, and pentaerythritol, said product having a mol ratio of acid to pentaerythritol of at least about 0.75, a ring and ball softening point of at least about 50° C., and an acid number less than about 40.

6. The ester of claim 5 wherein the mol ratio is between about 0.75 and 20.

7. The ester of claim 6 wherein the mol ratio is between about 0.75 and 2.5.

8. The ester of claim 6 wherein the ring and ball softening point is between about 100° and 200° C.

9. A rosin, alkyd, or polyester resin containing the ester of claim 1.

10. A rosin, alkyd, or polyester resin containing the ester of claim 3.

11. A rosin, alkyd, or polyester resin containing the ester of claim 5.

12. A rosin, alkyd, or polyester resin containing the ester of claim 6.

13. An ester of trimethylolacetic acid and trimethylolpropane, which ester is a solid at ambient temperature conditions, comprising the condensation product of said acid and said trimethylolpropane, said product having a mol ratio of acid to trimethylolpropane of at least about 1.75, a ring and ball softening point of at least about 50° C., and an acid number of less than about 40.

14. The ester of claim 13 wherein the mol ratio is between about 1.75 and 20.

15. The ester of claim 14 wherein the mol ratio is between about 1.75 and 2.5.

16. The ester of claim 15 wherein the ring and ball softening point is between about 100° and 200° C.

17. A rosin, alkyd, or polyester resin containing the ester of claim 13.

18. A rosin, alkyd, or polyester resin containing the ester of claim 15.

19. The ester of claim 1 wherein the acid number is less than about 20.

20. The ester of claim 3 wherein the acid number is less than about 20.

21. The ester of claim 5 wherein the acid number is less than about 20.

22. The ester of claim 7 wherein the acid number is less than about 20.

23. The ester of claim 13 wherein the acid number is less than about 20.

24. The ester of claim 15 wherein the acid number is less than about 20.

25. A method of preparing an ester of a sterically hindered polyhydroxymonocarboxylic acid and a polyhydroxy-containing component, which ester is a solid at ambient temperature conditions, comprising the condensation product of said acid selected from the group consisting of dimethylolpropionic acid, trimethylolacetic acid, and mixtures thereof, and said polyhydroxy-containing component selected from the group consisting of pentaerythritol, trimethylolethane, and mixtures thereof, said product having a mol ratio of acid to polyhydroxy-containing component of at least about 1.75, a ring and ball softening point of at least about 50° C., and an acid number of less than about 40, said method comprising;

reacting the polyhydroxymonocarboxylic acid and the polyhydroxy-containing component at a temperature of between about 80° C. and the decomposition temperature of the acid, in the presence of a catalytically effective quantity of an active sterically hindered carboxylic acid esterification catalyst to produce an ester.

26. A method of preparing an ester of a sterically hindered polyhydroxymonocarboxylic acid and a polyhydroxy-containing component, which ester is a solid at ambient temperature conditions, comprising the condensation product of said acid selected from the group consisting of dimethylolpropionic acid, trimethylolacetic acid, and mixtures thereof, and pentaerythritol, said product having a mol ratio of acid to pentaerythritol of at least about 0.75, a ring and ball softening point of at least about 50° C., and an acid number less than about 40, said method comprising:

reacting the polyhydroxymonocarboxylic acid and the pentaerythritol at a temperature of between about 80° C. and decomposition temperature of the acid, in the presence of a catalytically effective quantity of an active sterically hindered carboxylic acid esterification catalyst to produce an ester.

27. A method of preparing ester of trimethylolacetic acid and trimethylolpropane, which ester is a solid at ambient temperature conditions, comprising the condensation product of said acid and said trimethylolpropane, said product having a mol ratio of acid to trimethylolpropane of at least about 1.75, a ring and ball softening point of at least about 50° C., and an acid number of less than about 40, said method comprising:

reacting the trimethylolacetic acid and the trimethylolpropane at a temperature of between about 80° C. and the decomposition temperature of the acid, in the presence of a catalytically effective quantity of an active sterically hindered carboxylic acid esterification catalyst to produce an ester.

* * * * *